(12) United States Patent
Dodd et al.

(10) Patent No.: US 6,592,853 B2
(45) Date of Patent: *Jul. 15, 2003

(54) DENTIN DESENSITIZER CONTAINING STANNOUS FLUORIDE

(75) Inventors: Gregory P. Dodd, Hackensack, NJ (US); Kenneth J. Markowitz, Fanwood, NJ (US)

(73) Assignee: Block Drug Company, Inc., Jersey City, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/512,526

(22) Filed: Feb. 24, 2000

(65) Prior Publication Data

US 2002/0098155 A1 Jul. 25, 2002

Related U.S. Application Data

(60) Provisional application No. 60/123,611, filed on Mar. 10, 1999.

(51) Int. Cl.[7] .............................. A61K 7/16; A61K 7/18
(52) U.S. Cl. ........................................... 424/52; 424/49
(58) Field of Search ...................... 424/49–58

(56) References Cited

U.S. PATENT DOCUMENTS

| | | | |
|---|---|---|---|
| 3,863,006 A | | 1/1975 | Hodosh ........................ 424/49 |
| 4,296,096 A | * | 10/1981 | Pierce |
| 4,418,057 A | * | 11/1983 | Groat, I et al. |
| 4,533,544 A | * | 8/1985 | Groat, II et al. |
| 4,661,341 A | | 4/1987 | Benedict et al. |
| 4,842,847 A | * | 6/1989 | Amjad, I |
| 4,892,725 A | * | 1/1990 | Amjad, II |
| 5,017,363 A | | 5/1991 | Suhonen |
| 5,270,031 A | * | 12/1993 | Lim et al. |
| 5,597,552 A | * | 1/1997 | Herms, I et al. |
| 5,653,964 A | * | 8/1997 | Herms, II et al. |
| 5,674,474 A | * | 10/1997 | Fisher, I et al. |
| 5,690,912 A | * | 11/1997 | Fisher, II et al. |
| 5,693,314 A | * | 12/1997 | Campbell, I et al. |
| 5,716,600 A | * | 2/1998 | Zahradnik et al. |
| 5,843,409 A | * | 12/1998 | Campbell, II et al. |
| 5,871,715 A | * | 2/1999 | Singh |
| 5,932,192 A | | 8/1999 | Campbell et al. .............. 424/52 |
| 6,284,030 B1 | * | 9/2001 | Orlowski, I et al. .......... 106/35 |
| 6,365,134 B1 | * | 4/2002 | Orlowski, II et al. ......... 424/53 |

FOREIGN PATENT DOCUMENTS

WO  9427565  * 12/1994

OTHER PUBLICATIONS

Thrash et al Int. Dent. J. 44(1) Suppl. I : 107–118 Anhydrous Gel Products 0.4% Stennous Fluoride Occlude Dentinal Tubules and Reduce Pain of Dentin Sensitivity Abstracted in, 1994.*

ADA/FDI World Dental Congress, Orlando *Lanza Law* et al "In Situ Idiode Permeability of Root Dentin Following Use of Two $S_nF_2$ Products" (Gel–Kam © GK—0.4% Stawnous Flouride/Anhydroos Gel Occludes Dentinal Tubules, Sep./Oct. 1996.*

Horizon Dental Center "Gel–Kam" Scherer Labs, Inc Drug Database Gel–Kam Sensitivity Therapy Fluoride Topical Drugstore.Com Colgate Gel–Kam 0.4% Stannous Flourine Gel For Sensitive Teeth, 1999–2000.*

* cited by examiner

*Primary Examiner*—Shep K. Rose
(74) *Attorney, Agent, or Firm*—Nora Stein-Fernandez

(57) ABSTRACT

A desensitizing agent for the cleaning and treatment of sensitive teeth in which the essential desensitizing ingredient is a combination of a first desensitizing agent in an amount of about 0.1 to about 2 wt. % of $SnF_2$, and a second desensitizing agent in an amount of about 0.1 to about 20 wt. % of a water soluble or water swellable polyelectrolyte. Dentifrice compositions employing the desensitizing agent of the present invention surprisingly exhibit excellent organoleptic and flavor release properties.

2 Claims, No Drawings

DENTIN DESENSITIZER CONTAINING STANNOUS FLUORIDE

This patent application claims the filing date of provisional patent application Ser. No. 60/123,611 filed on Mar. 10, 1999.

BACKGROUND OF THE INVENTION

1. Field of the Invention

This invention relates to compositions and methods for the treatment of pain and discomfort associated with sensitive teeth.

2. Description of Related Art

Stannous fluoride ($SnF_2$), has been used in dentistry since the 1950's to treat various oral conditions. Topical application of $SnF_2$ consistently has shown dramatic reductions in dental caries activity with minimal side effect. $SnF_2$ has also been indicated clinically to be efficacious in the reduction of dentinal hypersensitivity. This latter therapeutic effect is believe to be attributable, to a large degree, to the stannous ion ($Sn^{2+}$) component of the salt.

U.S. Pat. No. 5,690,912 teaches that in order for the stannous ion to be efficacious in treating dentine hypersensitivity, it must be stable and freely available and not in chemical combination with other ingredients. The patent discloses oral hygiene preparations containing $SnF_2$ in a composition with 87–97 wt. % anhydrous glycerine and 2–10 wt % polyethylene glycol having an average molecular weight of 1000.

Besides $SnF_2$, other materials have been disclosed as active ingredients in the treatment of hypersensitive teeth. U.S. Pat. No. 3,863,006 discloses the use of potassium, sodium and lithium nitrates as desensitizing agents. U.S. Pat. No. 5,270,031 discloses the use of a water soluble or water swellable polyelectrolyte or partial salts thereof as a dental desensitization agent.

U.S. Pat. No. 5,693,314 teaches that attempts to include mixtures of a desensitizing agent such as $SnF_2$ with another desensitizing source such as potassium salts, i.e., potassium nitrate, in a single dentifrice composition are of limited effect. Additionally, prolonged contact between $Sn^{2+}$ and nitrate ion in a single dentifrice results in a reaction of these ions into potentially toxic materials. Thus, the solution is in keeping the two desensitizing sources separate from each other, and combining them for the first time only on the surface of the teeth, thus avoiding any appreciable formation of insoluble tin or reaction product of tin.

U.S. Pat. No. 5,932,192 restates earlier teachings that stannous compounds react with water and other common oral care ingredients to form insoluble tin. Further, stannous ions impart an astringent, bitter, sour metallic taste to dentifrices. The patent provides the same solution of a two-component composition of stannous salt and potassium salt, in which the water content within the potassium salt component is at least 44 wt. % and the overall water content is at least 22 wt. %, whereby the astringency, sourness and bitterness of the stannous salt is significantly reduced.

Applicants have found that there is no need to for dual component toothpastes with dual containers to keep the stannous fluoride compounds separate from other desensitizing agents in a desensitizing composition. We have surprisingly found that stannous fluoride as a desensitizing agent can be combined directly with another desensitizing agent in a dentifrice composition, without the cumbersome and costly manufacturing and packaging processes required in the prior art. In combining stannous fluoride directly with another desensitizing agent to further take advantage of the known anticaries and anti-microbial action of $SnF_2$, we have also surprisingly improved the physical properties of a gel dentifrice composition in its appearance. The desensitizing composition of the present invention also surprisingly exhibits excellent organoleptic and flavor release properties.

SUMMARY OF THE INVENTION

The invention provides a desensitizing agent comprising an anhydrous system containing stannous fluoride and at least another desensitizing agent, a cross-linked water soluble or water swellable polyelectrolytes or a partial salts thereof.

The invention further provides a method for treating dentinal sensitivity by administering a composition comprising an anhydrous system containing stannous fluoride and at least another desensitizing agent, water soluble or water swellable polyelectrolytes or a partial salts thereof.

DETAILED DESCRIPTION OF THE INVENTION

Besides the desensitizing agents, an essential component of the present invention is an orally acceptable dentifrice carrier. The carrier for the components of the present compositions can be any dentifrice vehicle suitable for use in the oral cavity. Such carriers include the usual components of toothpastes, creams, tooth powders, prophylaxis pastes, lozenges, gums, mouthwash concentrate and the like and are more fully described hereinafter. Toothpastes are the preferred systems.

First Desensitizing Component—Stannous Fluoride

Stannous fluoride is used as one of the desensitizing agents in the present invention. It is available in a powder form. Generally, the stannous fluoride in the various preparations of the present invention is between about 0.10 to 2% by weight, and preferably about 0.3 to about 1% by weight.

Second Desensitizing Component.

The second synergistic desensitizing agent of the present invention is water soluble or water swellable and contains functional groups capable of bearing a charge. The water soluble or swellable polymers are generally called polyelectrolytes, that is, polymers which bear one or more functional groups capable of bearing a charge in an aqueous medium. These polyelectrolytes can be anionic, cationic or amphoteric.

One example of an anionic functional group is the carboxylate group. This group is found in such polymers as polyacrylic acid, copolymers of acrylic acid and maleic acid, copolymers of methacrylic acid and acrylic acid, copolymers of alkyl vinyl ethers and maleic acid or anhydride, and the like. In the alkyl vinyl ether/maleic acid or anhydride copolymers, the alkyl group generally contains 1 to about 10 carbon atoms and is most preferably a methyl group. The copolymer can be produced using procedures well known in the art or commercially available forms can be employed. Polyacrylic acid can be obtained from B. F. Goodrich under the tradename Carbopol® as a cross-linked polyacrylic acid. These and other usable anionic polyelectrolytes are available from various other manufacturers. Another anionic functional group is the sulfonate group which is found for instance in sodium polystyrene sulfonate polymers.

The polyelectrolytes can contain cationic functional groups such as quaternized amines, imines, amides and alkyl ammonium groups. Examples include copolymers of vinyl pyrrolidone and dialkyl aminoalkyl methacrylates, chitosan, cationic celluloses and the like. A copolymer of vinyl pyrrolidone and dialkyl aminoalkyl methacrylate is available from International Specialty Products under the tradename Gafquat®.

Amphoteric polymers can also be used as a dentinal desensitizing agent. Examples include the aminoalkyl methacrylate and acrylates, copolymers of aminoalkyl acrylamides and acrylates, gelatin and the like.

The commercially available polymers are produced over a range of molecular weights. It is preferable to employ the highest molecular weight grade consistent with the viscosity of the formulation being prepared and concentration of the agent. A preferred polymer is a polyacrylic acid having a molecular weight of at least 500,000.

The second desensitizing agent can also be in the form of super-absorbent acrylic polymers, i.e., hydrogel forming polymers are water-absorbent, yet water-insoluble, cross-linked polymers that have been typically used in diapers, feminine hygiene articles and surgical dressings. Descriptions of super-absorbent polymers and their uses are found in U.S. Pat. Nos. 3,669,103 and 3,670,731. They are substantially water-insoluble, cross-linked, partially neutralized polymers, generally having a gel capacity of at least 50 grams of deionized water per gram at 20° C. and often at least 100 grams, 200 or more grams of water per gram dry weight of polymer at 20° C.

A preferred super-absorbent acrylic polymer is a water absorbent, water-insoluble, cross-linked acrylic polymer having a gel capacity of at least 50 grams deionized water per gram dry polymer at 20° C. The most preferred polymer is a sodium polyacrylate emulsion polymer sold by Allied Colloids under the trade designation DP6-6984.

The formulations will contain a second desensitizing agent in an amount which is generally from about 0.1% to 20% by weight of the polymer or its partial salts, with about 0.5–10% being preferred and about 1–5% most preferred. For any given concentration, viscosity 9 generally increases with molecular weight and for any given molecular weight, viscosity generally increases with concentration.

Anhydrous Base Component

It is desirable to include humectant material in the dentifrice composition of the present invention to keep it from hardening. Suitable humectants include glycerin, sorbitol, and other edible polyhydric alcohols such as polyethylene glycol at a level of from about 15% to about 98 wt. %. The humectant can be a mixture of humectants, such as glycerol and polyethylene glycol of molecular weight in the range of 200–1000, but other mixtures of humectants and single humectants may also be employed.

Optional Components.

In the present invention, the second desensitizing agent water soluble or water swellable polyelectrolyte functions as a thickening agent. However, other thickeners may still be added to give the final product the desired consistency. Inorganic thickeners may include fumed silicas such as Cabosil available from Cabot Corporation, and thickening silicas including those available from Crosfield Chemicals designated Sorbosil TC-15 or Sylox 15 from W. R. Grace. Organic thickeners of natural and synthetic gums as colloids may also be incorporated in the dentifrice composition of the present invention in which potassium salts are an ingredient. Examples of such thickeners are carrageenan (Irish moss), xanthan gum and sodium carboxymethyl cellulose, starch, polyvinylpyrrolidone, hydroxyethylpropylcellulose, hydroxybutyl methyl cellulose, hydroxypropyl methyl cellulose, and hydroxyethyl cellulose.

Abrasives may be incorporated in the compositions of the present invention. Preferred abrasives are siliceous materials, such as silica, and will normally have a mean particle size up to about 10 microns and a very high surface area e.g. in the range of 150–750 square meters/gram. Besides silica, other abrasives may also be employed, including sodium metaphosphate, potassium metaphosphate, tricalcium phosphate, calcium phosphate dihydrate, anhydrous dicalcium phosphate, calcium pyrophosphate, magnesium orthophosphate, trimagnesium phosphate, calcium carbonate, sodium bicarbonate, alumina trihydrate, aluminum silicate, zirconium silicate, calcined alumina and bentonite.

Suitable preservatives in this invention include benzoic acid, butylated hydroxyanisole (BHA), butylated hydroxytoluene (BHT), ascorbic acid, methyl paraben, propyl paraben, tocopherols and mixtures thereof.

Coloring agents in this invention are used in amounts effective to produce a dentifrice of the desired color. These coloring agents may be incorporated in amounts up to about 3% by weight of the dentifrice composition of the present invention. The coloring agents may also include natural food colors and dyes suitable for food, drug and cosmetic applications. A preferred opacifier, titanium dioxide, may be incorporated in amounts up to about 2.0 wt. %, preferably less than about 1.0% w/w of the composition.

The sweetener content will normally be that of an artificial or synthetic sweetener and the normal proportion thereof present will be in the range of 0.1 to 1% by weight, preferably 0.3 to 0.5% by weight. Anhydrous carbohydrate sweeteners include sorbitol, lycasin, and hydrogenated glucose syrup.

The flavors which may be used in the invention include natural and artificial flavors known in the dentifrice art. Suitable flavors include, but are not limited to, mints, such as peppermint, citrus flavors such as orange and lemon, artificial vanilla, cinnamon, various fruit flavors, and the like.

Preparation.

A dentifrice composition according to the present invention can be made by first combining the humectants, one or more sweeteners, flavors, and the desensitizing agents at a temperature sufficient to dissolve and mix all the components well, preferably from about 90° to 140° C. Abrasive, colors, flavors, and other optional components may be added and mixed in at the same time or subsequently in steps. A vacuum is pulled if necessary for deaeration.

The apparatus useful in accordance with the present invention comprises mixing apparatus well known in the dental art, and therefore the selection of the specific apparatus will be apparent to the artisan.

EXAMPLES

The following examples are provided in order to more fully describe and detail particular embodiments and formulations comprising the compositions of the present invention. They are for illustrative purposes only, and it is understood that minor changes and alterations can be made to these formulations and the processes for their preparation that are not contemplated thereby.

Test Methods:

For hypersensitivity tests, some of the prepared examples were tested using the method described by Pashley (J. Periodontology, Vol. 55, No. 9, p. 522, September 1984). This test measures the flow of fluid through a sliced dentin disc. A treatment that reduces the flow through the disc is an indication that the treatment can also result in reduced dentinal hypersensitivity for people using the treatment.

In this method, a caries free tooth is sliced to obtain a 0.4 to 0.6 mm thick dentin disc. The disc is mounted on a split chamber device. The initial flow of fluid through the disc is measured, and then the disc is treated by brushing with one of the desensitizing treatments. After brushing, the flow rate is again measured and the reduction in flow is calculated from these measurements.

Viscosity tests are conducted using a Haake viscometer. A viscosity of around 100,000 is optimal for a paste dentifrice. A viscosity of about 500,000 is considered to be undesirable for an oral therapeutic product.

In the "ribbon test" to test the extrudable consistency of the gel/paste compositions of the present invention, the compositions are first extruded as a ribbon onto the bristles of a toothbrush to see if they remain in stand-up position on the toothbrush without substantially sinking through the bristles. The ribbons are left standing over a period of at least three days to observe for phase separation.

In the "taste" test, the organoleptic qualities of the compositions in a toothpaste form were tested by a panel of users for "feel" as well as overall taste acceptability.

Examples 1–4

Desensitizing gel compositions were prepared (examples 1 and 2) and compared with commercial products in (examples 3 and 4). The ingredients are all in weight percent.

| Ingredidents | 1 | 2 | ELMAX ® Geleé | GELKAM ® |
|---|---|---|---|---|
| Stannous fluoride | 0.44 | 0.00 | 0.00 | 0.44 |
| Sodium fluoride | 0 | 0 | 2.21 | 0 |
| Amine fluoride | 0 | 0 | 3.319 | 0 |
| Anhydrous glycerin | 96.36 | 96.49 | — | — |
| Carbopol ® 980NF | 2 | 2 | — | — |
| Sodium saccharin | 0.2 | 0.2 | — | — |
| Sodium benzoate | 0.2 | 0.2 | — | — |
| Flavor mix | 1.2 | 1.2 | — | — |
| Reduced flow | 81.5 ± 9 (N + 4) | 88.1 ± 1.8 (N = 3) | 26.8 ± 27 (N = 8) | 26.6 + 19.1 (N = 8) |
| Viscosity (cp) | 108,000 | 540,000 | — | — |

"—"means it was not tested or measured.

As shown above, the viscosity of the present invention as shown above is surprisingly desirable for a gel toothpaste, as compared to the viscosity of the dentifrice composition having only one desensitizing agent of Example 2.

To determine the cosmetic (physical stability) of the present composition, tubed gel samples of Example 1 were "ribbon" tested. Excellent stand-up was observed after twenty minutes. No phase separation and continued stand-up was observed over a period of at least seventy-two hours. The samples were also tested by a panel of users, and a high rating was given for overall taste acceptability for the composition of the present invention.

What is claimed is:

1. An anhydrous gel or paste dental composition exhibiting improved stand-up and efficacy in treating hypersensitive teeth, comprising a first desensitizing agent which is $SnF_2$ in an amount of about 0.1 to about 2 wt. %, and a second desensitizing agent which is in the form of a cross-linked polyacrylic acid in an amount of about 0.1 to about 20 wt. %, and wherein said first desensitizing agent and second desensitizing agent are directly combined in the composition without the need for separating said first and second desensitizing agents prior to treating the hypersensitive teeth, said composition further comprising an anhydrous humectant selected from the group consisting of glycerin and sorbital, in an amount of about 15% to about 98 wt. %.

2. A method for desesitizing a sensitive tooth, comprising administering to said sensitive tooth an anhydrous gel or paste dental composition comprising a first desensitizing agent which is $SnF_2$ in an amount of about 0.1 to about 2 wt. %, and a second desensitizing agent which is which is in the form of a cross-linked polyacrylic acid in an amount of about 0.1 to about 20 wt. %, and wherein said first desensitizing agent and second desensitizing agent are directly combined in the composition without the need for separating said first and second desensitizing agents prior to treating the hypersensitive teeth, said composition further comprising an anhydrous humectant selected from the group consisting of glycerin and sorbital, in an amount of about 15% to about 98 wt. %.

* * * * *